United States Patent [19]
Kirby et al.

[11] 4,071,560
[45] Jan. 31, 1978

[54] DIAMINOALDITOLS USEFUL IN THE PREPARATION OF ANTIBACTERIAL ANTIBIOTICS AM31α, AM31β, AND AM31γ

[75] Inventors: Jane Parsons Kirby, New City; Donald Bruce Borders, Suffern, both of N.Y.

[73] Assignee: American Cyanamid Company, Stamford, Conn.

[21] Appl. No.: 775,505

[22] Filed: Mar. 8, 1977

Related U.S. Application Data

[60] Continuation-in-part of Ser. No. 719,226, Aug. 31, 1976, abandoned, which is a division of Ser. No. 559,998, March 19, 1975, Pat. No. 3,987,029, which is a continuation-in-part of Ser. No. 436,008, Jan. 23, 1974, abandoned.

[51] Int. Cl.$^2$ .............................................. C07C 91/12
[52] U.S. Cl. .............................. 260/584 R; 195/31 R; 195/80 R; 424/181; 536/4; 536/17; 536/18
[58] Field of Search ........................ 260/584 R, 501.2

[56] References Cited
U.S. PATENT DOCUMENTS

| | | | |
|---|---|---|---|
| 3,268,556 | 8/1966 | Hoeksema | 260/584 R X |
| 3,346,635 | 10/1967 | Bannister et al. | 260/584 R X |
| 3,723,617 | 3/1973 | Sutton | 260/210 R |
| 3,987,029 | 10/1976 | Kirby et al. | 260/584 R X |

Primary Examiner—Daniel E. Wyman
Assistant Examiner—John J. Doll
Attorney, Agent, or Firm—Edward A. Conroy, Jr.

[57] ABSTRACT

This disclosure describes a novel class of antibiotics, three of which have been designated AM31α, AM31β, and AM31γ and are produced in a microbiological fermentation under controlled conditions using a new strain of *Streptoverticillium netropsis*.

3 Claims, 2 Drawing Figures

INFRARED ABSORPTION SPECTRUM OF A MIXTURE OF AM31α, AM31β, AND AM31γ IN A KBr DISC

DIAMINOALDITOLS USEFUL IN THE PREPARATION OF ANTIBACTERIAL ANTIBIOTICS AM31α, AM31β, AND AM31γ

CROSS REFERENCE TO RELATED APPLICATIONS

This application is a continuation-in-part of our co-pending application Ser. No. 719,226, filed Aug. 31, 1976, now abandoned, which is a division of our application Ser. No. 559,998, filed Mar. 19, 1975, now U.S. Pat. No. 3,987,029, which is a continuation-in-part of our application Ser. No. 436,008, filed Jan. 23, 1974, now abandoned.

BRIEF SUMMARY OF THE INVENTION

This invention relates to new organic compounds and, more particularly, is concerned with novel antibiotics which may be represented by the following structural formula:

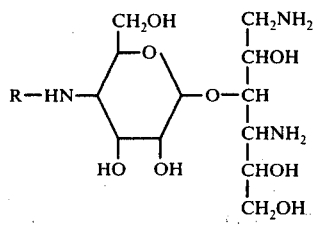

wherein R is hydrogen, formyl, or alkanoyl having up to 12 carbon atoms. The three antibiotics wherein R is hydrogen, acetyl, or propionyl in the above formula have been designated AM31α, AM31β, and AM31γ, respectively, and are produced by fermentation. Those compounds wherein R is formyl or alkanoyl in the above formula may be reaily prepared by formylating or alkanoylating antibiotic AM31α by standard methods well known in the art.

DETAILED DESCRIPTION OF THE INVENTION

Figure 1:
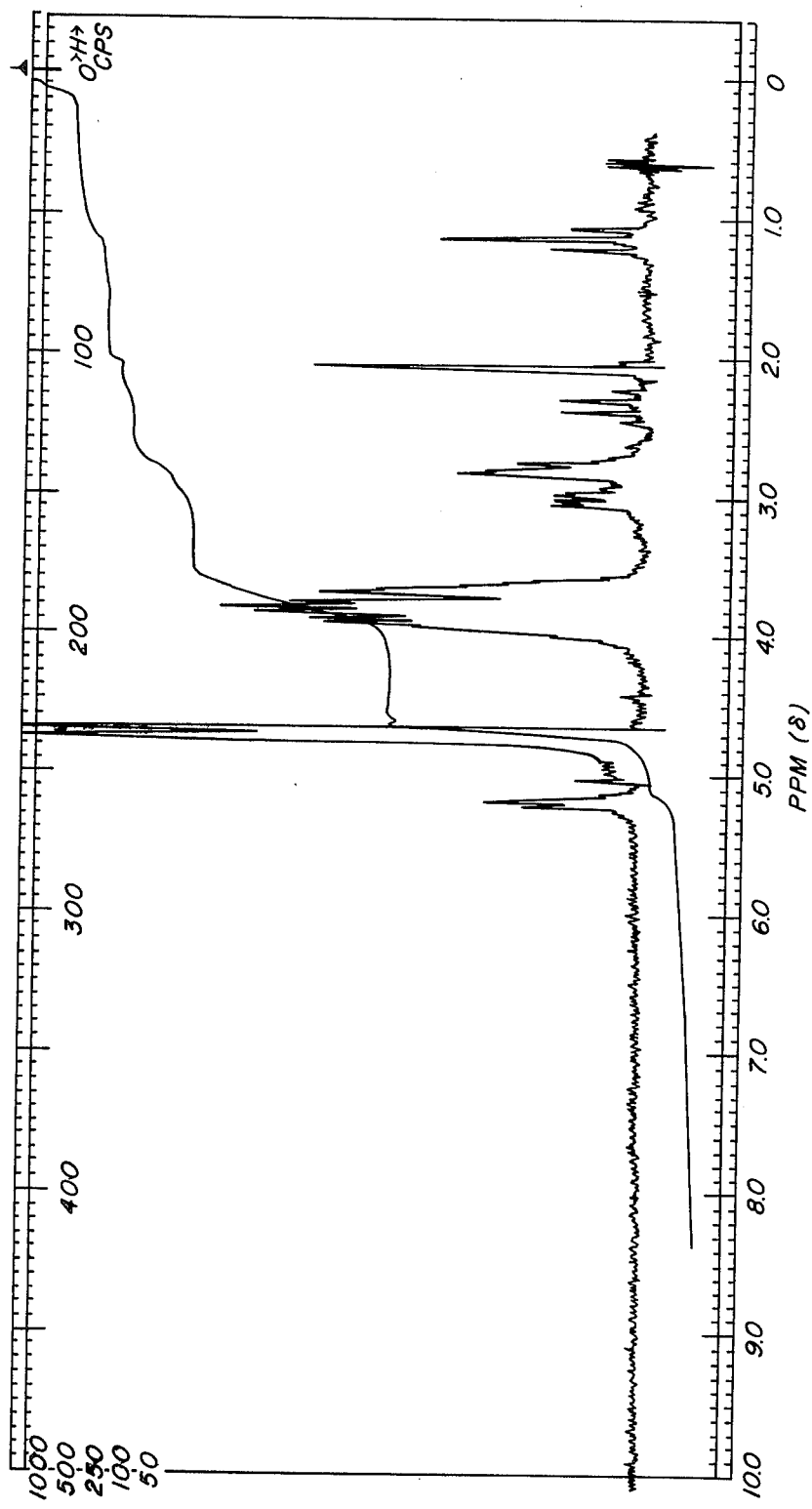

The new antibiotics designated AM31α, AM31β, and AM31γ are formed during the cultivation under controlled conditions of a new strain of *Streptoverticillium netropsis*. This new antibiotic-producing strain was isolated from a soil sample collected near Emma, Indiana. A viable culture of the new microorganism has been deposited with the Culture Collection Laboratory, Northern Utilization Research and Development Division, United States Department of Agriculture, Peoria, Illinois, and has been added to its permanent collection. It is freely available to the public in this depository under its accession number NRRL 5774. The description and identification of this new microorganism, maintained in the culture collection of the Lederle Laboratories Division, American Cyanamid Company, Pearl River, New York as Culture No. AM31, is fully set forth in U.S. Pat. No. 3,987,029, which is hereby incorporated by reference. It is to be understood that for the production of the new antibiotics AM31α, AM31β, and AM31γ, the present invention is not limited to NRRL 5774 or to microorganisms fully answering its growth and microscopic characteristics. In fact, it is desired and intended to include the use of mutants produced from NRRL 5774 by various means such as exposure to X-radiation, ultraviolet radiation, nitrogen mustard, actinophages, and the like.

Fermentation Process

Cultivation of the microorganism *Streptoverticillium netropsis* NRRL 5774 may be carried out in a wide variety of liquid culture media. Media which are useful for the production of these three antibiotics include an assimilable source of carbon such as starch, sugar, molasses, glycerol, etc., an assimilable source of nitrogen such as protein, protein hydrolysate, polypeptides, amino acids, corn steep liquor, etc., and inorganic anions and cations, such as sodium, potassium, calcium, sulfate, phosphate, chloride, etc. Trace elements such as boron, molybdenum, copper, etc., are supplied as impurities of other constituents of the medium. Aeration in tanks and bottles is provided by forcing sterile air through or onto the surface of the fermenting medium. Further agitation in tanks is provided by a mechanical impeller. An antifoaming agent, such as lard oil, may be added as needed.

Inoculum Preparation

Shaker flask inoculum of *Streptoverticillium netropsis* NRRL 5774 is prepared by inoculating 100 ml. of sterile liquid medium in 500 ml. flasks with scrapings or washing of spores from an agar slant of the culture. The following is an example of a suitable medium:

| | |
|---|---|
| Corn starch | 24 gm. |
| Bacto tryptone | 5 gm. |
| Yeast extract | 5 gm. |
| Beef extract | 3 gm. |
| Glucose | 1 gm. |
| Water to | 1000 ml. |

The pH is adjusted to 7.0 with NaOH.

The flasks are incubated at a temperature from 25°–29° C., preferably 28° C., and agitated vigorously on a rotary shaker for 30 to 48 hours. These 100 ml. portions of inoculum are used to inoculate one and twelve liter batches of ths same medium in 2 liter and 20 liter glass fermentors at 28° C. The inoculated mash is aerated with sterile air while growth is continued for 40 to 55 hours. These batches are used to inoculate tank fermentors.

Tank Fermentation

For the production of antibiotics AM31α, AM31β, and AM31γ in tank fermentors the following medium is preferably used:

| | |
|---|---|
| Soy flour | 40 gm. |
| Molasses | 20 gm. |
| Glucose | 10 gm. |
| Calcium carbonate | 3 gm. |
| Water to | 1000 ml. |

Each tank is inoculated with 3 to 10% of inoculum made as described above. Aeration is supplied at the rate of 0.2 to 0.8 liter of sterile air per liter of broth per minute and the fermenting mixture is agitated by an impeller driven at 200 to 400 rpm. The temperature is maintained at 25°–29° C., usually at 28° C. The fermentation is ordinarily continued for 80 to 100 hours, at which time the mash is harvested.

Isolation of AM31α, AM31β, and AM31γ as a Mixture

After the fermentation is completed, the harvested mash is filtered and the filtrate, at pH 7.8, is passed through a 5 liter Amberlite IRC-50 ® (a methacrylate acid-divinyl benzene ion exchange resin) ($NH_4+$) column at a flow rate of 250 ml./minute. After the column is washed with 25 liters of deionized water, the antibiotic activity is eluted with 30 liters of 2N $NH_4OH$ and detected by the conventional disc agar diffusion assay against *Klebsiella pneumoniae*. The 30 liters of eluate at pH 11.7 is reduced to 2 liters and adjusted to pH 8.1 with 0.1N HCl. The antibiotics in this concentrate are adsorbed onto an Amberlite CG-50 ® (a methacrylic acid-divinyl benzene ion exchange resin) ($NH_4+$) column and eluted with 1.5N $NH_4OH$. The column eluate is concentrated to 65 ml. of an orange viscous syrup on a rotary evaporator. This concentrate is passed through a Dowex 1-X2 ® (a trimethylbenzylammonium polystyrene cross linked with 2% divinyl benzene) ($OH^-$) (50-100 mesh column and the column is developed with water. The bioactive effluent is divided into 2 major fractions based on visible color and bioactivity. One fraction (1) contains a mixture of AM31α,β, and γ and as white powder that is essentially free of unwanted impurities. The fraction, obtained in a liquid state because of impurities, may be further processed to yield more antibiotic mixture. This liquid fraction is passed through a Dowex 1-X2 ® ($OH^-$) (200-400 mesh) column. The column is developed with water and 3 major fractions are obtained, two (II and IV) as a white powder and one (III) as a thick yellow syrup. This yellow syrup is further purified by adsorption on a Dowex 50-X8 ® (a sulfonated polystyrene cross linked with 8% divinyl benzene) (H+) column. The column is rinsed with 250 ml. of water and the antibiotics are eluted with 500 ml. of 1.5N $NH_4OH$. Two bioactive fractions are obtained in the 60-70 ml. and 290-700 ml. portions of column eluate. Each fraction is reduced to a small volume on a rotary evaporator and then freeze-dried yielding a fine white powder (V) and a white hygroscopic powder (VI). All of the fractions contain mixtures of the three components.

Separation of AM31α, AM31β, and AM31γ by Paper Chromatography

The components are differentiated from each other by paper chromatography using 1-butanol saturated with water to which 2% p-toluenesulfonic acid is added. The $R_f$ values are: 0.61; 0.43; and 0.31, obtained by minhydrin.

In vitro Activity

The mixture of antibiotics AM31α, β, and γ are active against a wide variety of gram positive and gram negative bacteria as determined by the standard agar-well diffusion technique. The results of such a test on the complex of the three components appear in Table I below.

TABLE I

| Name of Organism | Inhibition Zone (mm)* |
|---|---|
| *Bacillus cereus* (Waksman) | 2.9 |
| *Klebsiella pneumoniae* (Friedlanders) | 5.8 |
| *Alcaligenes* sp. ATCC 10153 | 4.1 |
| *Bacillus subtilis* (Stansly R-78) | 5.8 |
| *Bacillus subtilis* (Resistant to Streptothricin) (Stansly R-76) | 1.0 |
| *Mycobacterium smegmatis* (#607) | 2.6 |
| *Staphylococcus aureus* (resistant to tetracycline) | 2.5 |
| *Escherichia coli* (Parke Davis) | 4.0 |
| *Escherichia coli* (resistant to chloramphenicol) | 7.3 |
| *Staphylococcus aureus* 209P (resistant to erythromycin) | 6.5 |
| *Corynebacterium xerosis* NRRL B-1397 | 8.5 |
| *Salmonella gallinarum* #605 | 7.3 |
| *Staphylococcus aureus* (Smith) | 5.3 |
| *Klebsiella pneumoniae* (AD) | 9.2 |
| *Pseudomonas aeruginosa* ATCC 10145 | 4.6 |
| *Escherichia coli* (Upjohn Culture) | 4.8 |
| *Aerobacter aerogenes* | 5.2 |
| *Proteus mirabilis* | 1.6 |
| *Salmonella typhosa* ATCC 6539 | 7.4 |
| *Staphylococcus aureus* ATCC 14154 | 1.3 |
| *Escherichia coli* 311 | 5.0 |
| *Pseudomonas aeruginosa* PA7 | 3.6 |

*Zone value given as distance from edge of well to outer edge of inhibition zone.

In vivo Results

A mixture containing the three antibacterial components AM31α, AM31β, and AM31γ is active in vivo against a variety of organisms. These new antibacterials are thereby potentially useful as therapeutic agents in treating bacterial infections in mammals. These new antibacterials can be expected to be usefully employed for treating or controlling bacterial infections by parenteral administration. The usefulness of these new antibacterial agents is demonstrated by their ability to control systemic lethal infections in mice. A mixture of these three new antibiotics shows high in vivo antibacterial activity in mice against *Escherichia coli*, *Salmonella typhosa* and *Klebsiella pneumoniae* when administered by a single subcutaneous dose to groups of Carworth Farms CF-1 mice, weighing about 20 gm., infected intraperitoneally with 0.5 ml. of the indicated broth dilution of 5 hour cultures of the following organisms: *Escherichia coli*, $10^{-3}$; *Salmonella typhosa* undiluted; *Klebsiella pneumoniae*, $10^{-4}$, Table II below, illustrates the in vivo antibacterial activity of a mixture of AM31α, AM31β, and AM31γ against these three bacteria.

TABLE II

| | Alive/Total Mice Treated 7 Days After Infection |
|---|---|
| Single Subcutaneous Dose mg./kg. | *Escherichia coli* |
| 512 | 2/2 |
| 256 | 2/2 |
| 128 | 2/2 |
| 64 | 2/2 |
| 32 | 0/2 |
| Infected non-treated controls | 2/10 |
| Single Subcutaneous Dose Mg./kg. | *Salmonella typhosa* |
| 512 | 2/2 |
| 256 | 2/2 |
| 128 | 2/2 |
| 64 | 0/2 |
| Infected non-treated controls | 0/10 |
| Single Subcutaneous Dose mg./kg. | *Klebsiella pneumoniae* |
| 512 | 2/2 |
| 256 | 2/2 |
| 128 | 0/2 |

TABLE II-continued

| | Alive/Total Mice Treated 7 Days After Infection |
|---|---|
| 64 | 0/2 |
| Infected non-treated controls | 0/10 |

This invention will be described in greater detail in conjunction with the following specific examples.

EXAMPLE 1

Inoculum Preparation

A typical sterile medium used to grow the primary inoculum was prepared according to the following formula:

Corn starch . . . 24 gm.
Bacto tryptone . . . 5 gm.
Yeast extract . . . 5 gm.
Beef extract . . . 3 gm.
Glucose . . . 1 gm.
Water to . . . 1000 ml.

The pH was adjusted to 7.0 with NaOH

Washed or scraped spores from an agar slant of *Streptoverticillium netropsis* NRRL 5774 were used to inoculate two 500 ml flasks containing 100 ml. each of the above sterile medium. The flasks were placed on a rotary shaker and agitated vigorously for 48 hours at 28° C. The resulting flask inoculum was transferred to a 5 gallon glass fermentor containing 12 liters of the same sterile medium. The inoculum mash was aerated with sterile air while growth was carried out for 48 hours at 28° C., after which the contents were used to seed a 300 liter tank fermentor.

EXAMPLE 2

Fermentation

A fermentation medium was prepared according to the following formula:

Soy flour . . . 40 gm.
Molasses . . . 20 gm.
Glucose . . . 10 gm.
Calcium carbonate . . . 3 gm.
Water to . . . 1000 ml.

Twelve liters of inoculum, prepared as described in Example 1, were used to inoculate 300 liters of the above sterilized fermentation medium. The fermentation was carried out for 89 hours at 28° C. with an aeration rate of 0.5 liter of air/liter of mash/minute. The mash was agitated by an impeller driven at 300 rpm. The mash was harvested.

EXAMPLE 3

Isolation of a Mixture of AM31α, AM31β, and AM31γ

A 300 liter portion of whole harvest mash, prepared as described in Example 2, was filtered. The filtrate, having a pH of 7.8, was passed through a 5 liter Amberlite ® IRC-50 ($NH_4+$) column, 4 × 60 inches, at a flow rate of 250 milliters per minute. The column was washed with 25 liters of deionized water. The antibiotic activity was eluted with 30 liters of 2N $NH_4OH$ and detected by the disc agar diffusion assay against *Klebsiella pneumoniae*. The 30 liter eluate at pH 11.7 was reduced to 2 liters and adjusted to pH 8.1 with 0.1N HCl. One liter of this concentrate was adsorbed on an Amberlite ® CG-50 ($NH_4^+$) 3 × 52 cm. column and eluated with 500 ml. of 1.5N $NH_4OH$. A duplicate run was made with the remaining one liter concentrate and the eluates from the two runs were combined and concentrated on a rotary evaporator to 65 ml. of an orange viscous syrup. This 65 ml. concentrate was passed through a Dowex ® 1-X2 ($OH^-$) (50-100 mesh) 2 × 54 cm. column and the column was developed with water. The bioactive effluent was divided into two fractions based on visible color and bioactivity. One fraction was recovered from 735-1200 ml. of column effluent. It was freeze dried to give 132 mg. of a white powder (I). The other fraction was from 270-734 ml. of column effluent. When this was freeze dried it remained in a liquid state, due to impurities. The liquid fraction was dissolved in water and the solution was passed through a Dowex ® 1-X2 ($OH^-$) (200-400 mesh) 1.5 × 21 cm. column. As the column was developed with water, 3 major fractions were obtained with the indicated elution volumes: Fraction II, 55-114 ml.; Fraction IV, 361-775 ml.; and Fraction III, 115-360 ml. of column effluent. Fractions II and IV were freeze-dried to give 4.76 gm. and 215 mg. of white powder, respectively. Fraction III was concentrated to 75 ml. of yellow syrup which was adsorbed on a Dowex ® 50-X8 (H+) 3 × 30 cm. column. This column was rinsed with 250 ml. of water and then eluted with 500 ml. of 1.5N $NH_4OH$. Two bioactive fractions were obtained in the 60-70 ml. and 290-700 ml. portions of the column effluent. Each fraction was reduced to a small volume on a rotary evaporator, freeze-dried and the solids were recovered, yielding 685 mg. of fine white powder (Fraction V) and 6.78 gm. of white hygroscopic powder (Fraction VI). Total yield, 12.572 gm.

Figure 2:
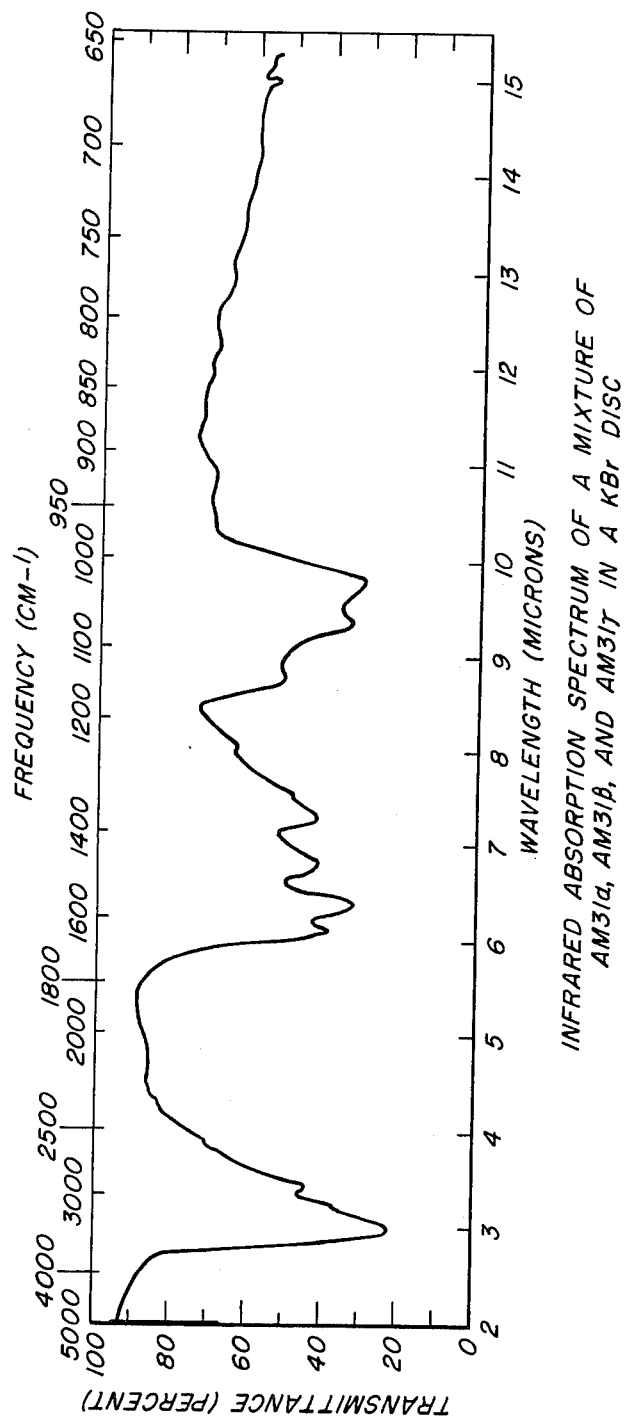

Infrared and nuclear magnetic resonance spectra suggested that the above fractions were all mixtures with approximately the same composition of α,β and γ components. Fraction II had $[\alpha]_D^{25°} = + 85.0° \pm 2.4°$ (C 0.41, $H_2O$). Anal. Found: C, 42.03%, H, 8.08%, N, 10.47%, Nuclear magnetic resonance and infrared spectra of a mixture of components are given in FIGS. 1 and 2, respectively, of the accompanying drawings.

EXAMPLE 4

Preparation of N-acetyl-O-trimethylsilyl Derivative of Antibiotic AM31 Complex The N-acetyl-O-trimethylsilyl derivative of the antibiotic AM31 complex was prepared in the following way for mass spectrum characterization. Four milligrams of AM31 complex was mixed with 0.50 ml. of methanol and 0.30 ml. of acetic anhydride. The solution was allowed to remain overnight at room temperature. The N-acetylated derivative was precipitated with 3-4 ml. of diethyl ether, washed several times with diethyl ether and dried in a desiccator. The O-trimethylsilyl derivative was then made by adding 0.5 ml. of TRI-SIL ® (a ready mix formula containing trimethylchlorosilane from Pierce Chemical Company, Rockford, Ill.). The silylation proceeded in a desiccator for 2 hours at room temperature after which the excess reagent was removed under vacuum. The residue was redistributed in benzene. The benzene-soluble material was separated from any residual solids and the solution was evaporated to a residue in a stream of nitrogen. The data for the mass spectrum of the N-acetyl-O-trimethylsilyl derivative are given in Tables III and V. The mass spectrum of the degradation product of AM31 complex, N-acetyl-O-trimethylsilyl derivative of the diaminodideoxyalditol is given in Table IV.

TABLE III

High Resolution Mass Spectral Data for N-Acetyl-O-Trimethylsilyl Derivative of AM31 Complex

| Observed | Exact Mass Calculated | Composition |
|---|---|---|
| 898.4324 | 898.4408 | $C_{36}H_{80}N_3O_{11}Si_6$ |
| 884.4238 | 884.4252 | $C_{35}H_{78}N_3O_{11}Si_6$ |
| 694.3380 | 694.3406 | $C_{28}H_{60}N_3O_9Si_4$ |
| 635.2995 | 635.3035 | $C_{26}H_{55}N_2O_8Si_3$ |
| 581.2909 | 581.2929 | $C_{23}H_{63}N_2O_7Si_4$ |
| 420.2056 | 420.2057 | $C_{17}H_{38}N_1O_5Si_3$ |

TABLE IV

High Resolution Measurements of N-Acetyl-O-Trimethylsilyl Derivative of Diaminodideoxyalditol (the degradation product of AM31 Complex)

| Observed | Exact Mass Calculated | Composition |
|---|---|---|
| 537.2668 | 537.2659 | $C_{21}H_{49}N_2O_6Si_4$ |
| 378.1952 | 378.1942 | $C_{15}H_{36}N_1O_4Si_3$ |
| 347.1822 | 347.1818 | $C_{14}H_{31}N_2O_4Si_2$ |
| 288.1450 | 288.1450 | $C_{12}H_{26}N_1O_3Si_2$ |
| 276.1421 | 276.1450 | $C_{11}H_{26}N_1O_3Si_2$ |
| 217.1081 | 217.1080 | $C_9H_{21}O_2Si_2$ |
| 198.0949 | 198.0959 | $C_9H_{16}N_1O_2Si$ |
| 186.0934 | 186.0950 | $C_8H_{16}N_1O_2Si$ |
| 174.0929 | 174.0950 | $C_7H_{16}N_1O_2Si$ |

TABLE V

Relative Abundance of Selected Ions Observed in Gas Chromatography/Mass Spectrum Analysis or N-Acetyl-O-Trimethylsilyl Derivative of AM31 Complex

| α and ν Components | | βComponent | |
|---|---|---|---|
| Ion (m/e) | Relative Abundance % | Ion (m/e) | Relative Abundance % |
| 174 | 25 | 174 | 20 |
| 186 | 50 | 186 | 35 |
| 276 | 3.5 | 276 | 3.5 |
| 420 | 100 | 434 | 100 |
| 581 | 2.5 | 581 | 2.5 |
| 635 | 32.5 | 649 | 22.5 |
| 694 | 8.5 | 708 | 7.5 |
| 884 | 6.0 | 898 | 4.0 |

These spectra were obtained with a Varian CH7 Gas Chromatography/Mass Spectrum with resolution M/ΔM 2000, ionizing voltage 70ev, and source temperature 200° C. Gas chromatography conditions were as follows: The column for the gas chromatography was 6 feet long. The support was 0.7% OV-1 on glass Chrom Q (mesh size 100-200). The column temperature was 230° C., injection port temperature 250° C., and detector temperature 210° C. The carrier gas was nitrogen. The retention times of the components were 24 minutes and 27.4 minutes.

EXAMPLE 5

Paper Chromatographic Separation of Antibiotic Components

The three components of the antibiotic mixture were differentiated using 1-butanol saturated with water to which 2% p-toluenesulfonic acid was added. The $R_f$ values for the components are 0.61, 0.43, and 0.31 as obtained by ninhydrin.

EXAMPLE 6

Preparation and Identification of Diaminoalditol Fragment of Antibiotic AM31 Complex A 100 mg. sample of Antibiotic AM31 was heated in 5 ml. of 6N HCl for 16 hours at 140° C. The resulting hydrolysate was filtered to remove considerable black precipitate, evaporated to a residue and dissolved in one ml. of water. This solution was poured onto a 1 × 2 cm. Dowex® 1-X2 (OH⁻) column (200-400 mesh), followed by 5 bed volumes of water. A dark brown hygroscopic solid (33.9 mg.) was recovered on freeze-drying the column effluent. A 10 mg. portion was used to prepare an N-acetyl-O-trimethylsilyl derivative for mass spectral studies as follows: Ten mg. of the product was mixed with 1.25 ml. of methanol and 0.75 ml. of acetic anhydride and allowed to remain overnight at room temperature. The N-acetylated compound was precipitated with 3-4 ml. of diethyl ether, washed several times with diethyl ether, dried in a desiccator and silyated with Tri-Sil® (a ready mix formula of trimethyl chlorosilane from Pierce Chemical Company, Rockford, Ill.). The silylation proceeded in a desiccator for 2 hours at room temperature after which the reagent was removed under vacuum and the residue was redistributed in benzene. The benzene-soluble material was separated from any residual solids and the solution was evaporated to a clear resin in a stream of nitrogen.

The structure and absolute configuration of the diaminoalditol was established through X-ray analysis of the dihydrochloride salt ($C_6H_{16}N_2$ ₀₄.2HCl.H₂O). Crystals grown from a wet ethanol/methanol mixture are orthorhombic, a = 13.222(9) b = 13.378(9) c = 6.845(3)A space group $P2_12_12_1$ (Z = 4); $d_m$ = 1.467 gm cm⁻³ (by flotation in CCl₄/hexane), $d_c$ = 1.486 gm cm⁻³. A crystal approximately 0.40 × 0.30 × 0.25 mm. was used to collect 966 independent observed reflections using the θ/2θ scan method with nickel filtered CuKα radiation; absorption corrections were not applied. The structure was solved by the MULTAN direct phase determination method and refined by least-squares methods with isotropic and anisotropic temperature parameters to R = 0.050. All hydrogens were located in difference maps and were refined isotropically. The absolute configuration was found by using the anomalous dispersion effect of chlorine. At the end of isotropic refinement (without dispersion) the R factor for nonhydrogens for the chosen configuration was R = 0.102; for the opposite configuration the value was R − 0.106.

The diaminoalditol forms acid-addition salts with a variety of organic and inorganic salt-forming reagents. Thus, acid-addition salts, formed by admixture of the diaminoalditol base with one or two equivalents of an acid, suitably in a neutral solvent, are formed with such acids as sulfuric, phosphoric, hydrochloric, hydrobromic, nitric, citric, lactic, tartaric, acetic, benzoic, and related acids. For purposes of this invention, the diaminoalditol free base is equivalent to its acid-addition salts.

EXAMPLE 7

Preparation and Identification of 4-Glucosamine Fragment of Antibiotic AM31

A 5 mg. portion of antibiotic AM31 was dissolved in 3 ml. of 3N HCl and heated in a sealed vial at 100°-110° C. for 5 hours. The product was evaporated to a residue which was redissolved in water and evaporated to remove HCl fumes. The residue was dissolved in 0.5 ml. of water and spotted onto sheets of Whatman #1 paper. The papergrams were developed by the descending technique and the solvent allowed to drip off the sheets. The AM31 hydrolysate had a component not differentiated from glucosamine by mobility and color reactions in the following systems: 1-butanol:pyridine:water (6:4:3), 11.0 cm. distance from origin, ethyl acetate:pyridine:water (72:20:23), 1.5 cm. distance from origin. Zones were detected by ninhydrin and the Tollens reagent.

Methanolysis of the antibiotic complex in 1.5N methanolic HCl at 100° C. for 30 minutes in a sealed vial yielded both the sugar, as a methylglycoside, and the diaminoalditol. The positional and tentative stereoisomeric form of the hexosamine was deduced from $^{13}$C nmr and comparative studies of the N-acetyl-O-trimethylsilyl derivative of the AM31 sugar methylglycoside with the corresponding derivatives of authentic 2-, 3-, 4- and 6-glucosamines. No significant pH shifts were observed in the $^{13}$C nmr for the anomeric carbon of the α-component; therefore, a 2-aminosugar was excluded. The gc retention time and ms fragmentation patterns (Table VI) of the AM31 sugar derivative were essentially identical to those of 4-glucosamine and significantly different from those of the other glucosamines when all samples were run under the same conditions.

TABLE VI

Gc-ms Data for Glucosamine Derivatives[a]

| Glucos- amine[b] isomer | Relative abundance[c] m/e | | | | | | | Retention Time[d] (min.) |
|---|---|---|---|---|---|---|---|---|
| | 73 | 146 | 173 | 186 | 204 | 316 | 436 (M-15) | |
| 2 | 100 | 3 | 83 | 29 | 40 | 3 | 6 | 14.5 |
| 3 | 100 | 21 | 95 | 2 | 6 | 2 | 9 | 13.3, 13.6[e] |
| 4 | 100 | 45 | 40 | 49 | 79 | 16 | 20 | 14.4, 14.6[e] |
| 6 | 82 | 54 | 43 | 10 | 100 | 10 | 5 | 16.1, 16.8[e] |
| X | 100 | 40 | 38 | 43 | 71 | 14 | 18 | 14.4, 14.6[e] |

[a]N-acetyl-O-trimethylsilyl derivatives of methylglycosides.
[b]2-,3-,4-, and 6-glucosamine and the AM31 sugar (X) derivatives.
[c]Abundances shown for selected ions.
[d]1.84 m. × 2 mm.glass column, SP2250 (Supelco); 140° C., Δt = 6 °/min. to 280 °; He, 35 ml./min.
[e]Two peaks corresponding to α and β methylglycosides.

EXAMPLE 8

Preparation of AM31β from the Diaminoalditol

The N,N'-diethoxycarbonyldiaminoalditol (I) is prepared from the diaminoalditol (obtained from the antibiotic hydrolyzate) by a procedure essentially the same as that employed by Nishimura et al. [Bull. Chem. Soc. Japan 43,2960 (1970)] to prepare N,N'-diethoxycarbonyl-2-deoxystreptamine. To a solution

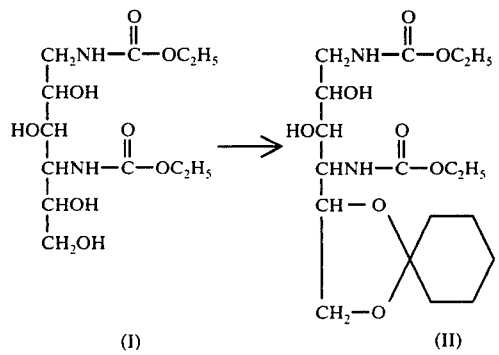

of 5.0g. of (I) in dry dimethylformamide is added 500 mg. of anhydrous p-toluenesulfonic acid and 10 ml. of dry 1,1-dimethoxycyclohexane. The resulting solution is stirred at 50° C. in vacuo (33 Torr.) for two hours and then evaporated to a residue which is mixed vigorously with ethyl acetate and a saturated aqueous solution of barium hydroxide. The organic layer is separated, washed with water, and evaporated to the crude mono-O-cyclohexylidene-N,N'-diethoxycarbonyldiaminoalditol (II). Methyl 4-propionamido-4-deoxy-α-D-glucopyranoside is prepared by reacting a methanolic solution of methyl 4-amino-4-deoxy-α-D-glycopyranoside [Naganawa et al., J. Antibiotics XXVII, 145 (1974)] with propionic anhydride. This product is benzylated with benzyl chloride in the presence of sodium hydride to afford the benzylated derivative which is converted to 2,3,6-tri-O-benzyl-N-benzyl-4-propionamido-4-deoxy-α-D-glucopyranosyl chloride (III) by successive acetolysis and chlorination. An anhydrous solution of 2.25 g. of (III) in 30 ml. of benzene is added to a suspension of 0.68 g. of mercuric cyanide, 5.4 g. of Drierite, and 1.65 g. of (II) in 10 ml. of dioxane and the mixture is stirred vigorously at 100° C. for 10 hours to obtain the condensation product (IV). This material is treated with

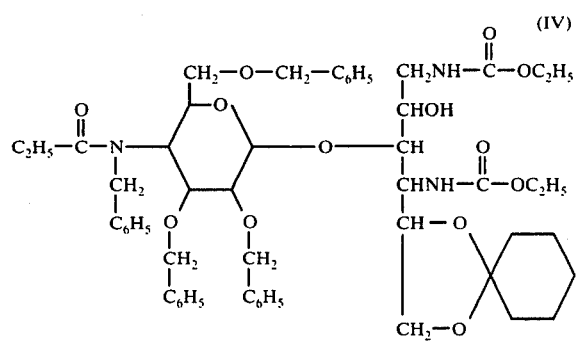

50% acetic acid in methanol at steam bath temperature to remove the cyclohexylidene group; hydrogenated in a mixture of dioxane:water:conc. hydrochloric acid (20:4:1) over palladium black with occasional addition of water to remove the benzyl groups; and then stirred overnight at room temperature with saturated aqueous barium hydroxide to remove the carbethoxy groups. The resulting mixture contains the antibiotic AM31β which can be purified by ion exchange chromatography on Amberlite ® IRC-50 (NH$_4$+) or on Dowex ® 50-X8 (NH$_4$+) as previously described for the natural antibiotic.

We claim:
1. A compound selected from the group consisting of a diaminoalditol of the formula:

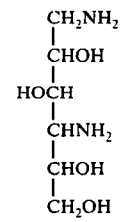

and the acid-addition salts thereof.
2. The compound in accordance with claim 1 as the free base.
3. The compound in accordance with claim 1 as the dihydrochloride salt.

* * * * *